United States Patent [19]
Kelly et al.

[11] Patent Number: 5,827,058
[45] Date of Patent: Oct. 27, 1998

[54] CARRIER FOR SUPPORTING ORTHODONTIC BRACKETS

[75] Inventors: John S. Kelly, Arcadia; Russell A. Jordan, Rancho Cucamonga; Randall E. Adam, Sierra Madre, all of Calif.

[73] Assignee: Minnesota Mining & Manufacturing Co., St. Paul, Minn.

[21] Appl. No.: 947,095

[22] Filed: Oct. 8, 1997

[51] Int. Cl.$^6$ .................................................. A61C 3/00
[52] U.S. Cl. .............................. 433/9; 206/63.5; 206/368
[58] Field of Search ..................... 433/8, 9; 206/63.5, 206/368, 369, 460, 461, 813

[56] References Cited

U.S. PATENT DOCUMENTS

| | | | |
|---|---|---|---|
| 4,978,007 | 12/1990 | Jacobs et al. | 206/469 |
| 5,015,180 | 5/1991 | Randklev | 433/9 |
| 5,183,403 | 2/1993 | Masuhara et al. | 433/9 |
| 5,221,202 | 6/1993 | James | 433/9 |
| 5,328,363 | 7/1994 | Chester et al. | 433/9 |
| 5,350,059 | 9/1994 | Chester | 433/9 |
| 5,538,129 | 7/1996 | Chester et al. | 206/63.5 |
| 5,552,177 | 9/1996 | Jacobs et al. | 427/2.29 |
| 5,575,645 | 11/1996 | Jacobs et al. | 433/9 |
| 5,653,588 | 8/1997 | Moschik | 433/8 |
| 5,697,780 | 12/1997 | Tuneberg et al. | 433/9 |

*Primary Examiner*—Nicholas D. Lucchesi
*Attorney, Agent, or Firm*—James D. Christoff

[57] ABSTRACT

An orthodontic assembly includes one or more orthodontic brackets that are releasably received in a tubular carrier. The carrier has arms with outer end sections that are spaced apart from each other to present a channel therebetween. The outer end sections of the arms are received in occlusal and gingival recesses of each bracket in order to support the bracket in suspended relation. The carrier is particularly useful for holding brackets during a manufacturing operation or during transport of the brackets from manufacturing operation to another. The carrier is also useful for supporting brackets in a package for shipment to the end user, especially when the brackets are precoated with a layer of adhesive.

28 Claims, 8 Drawing Sheets

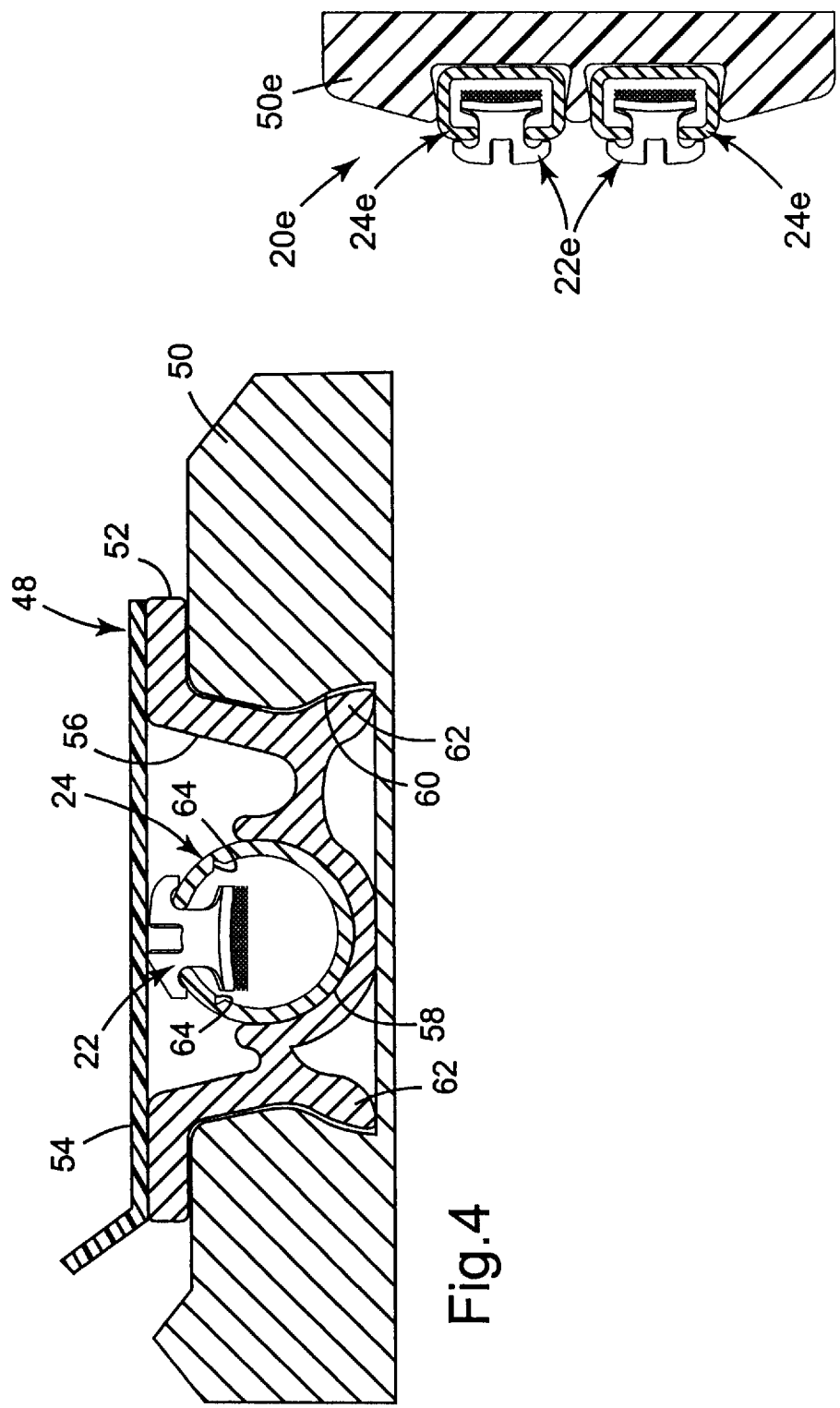

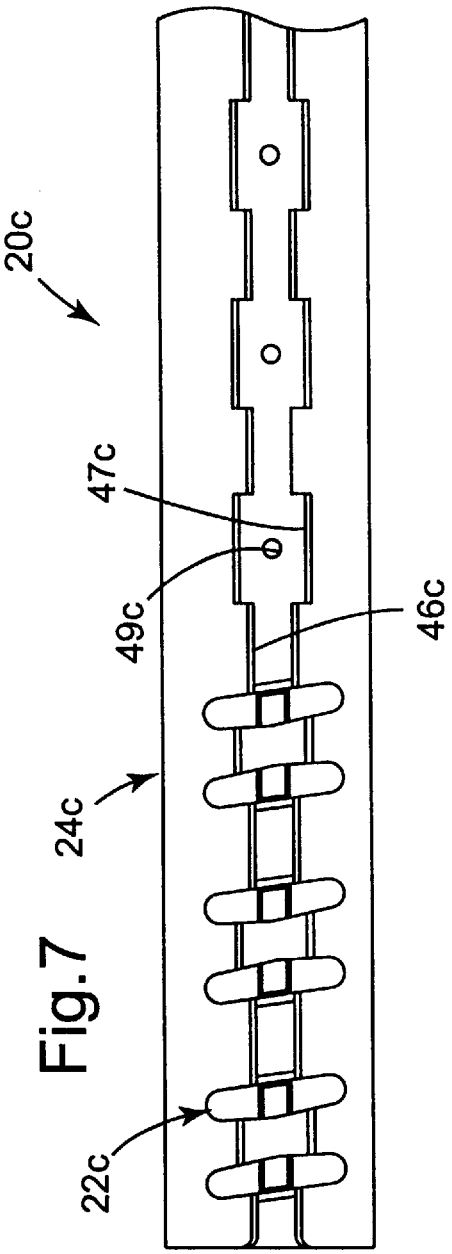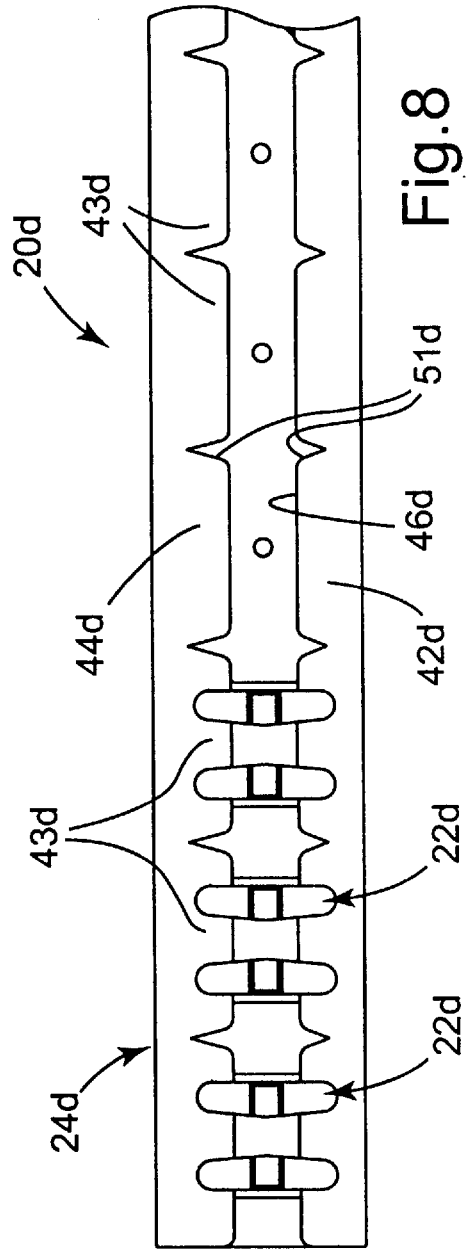

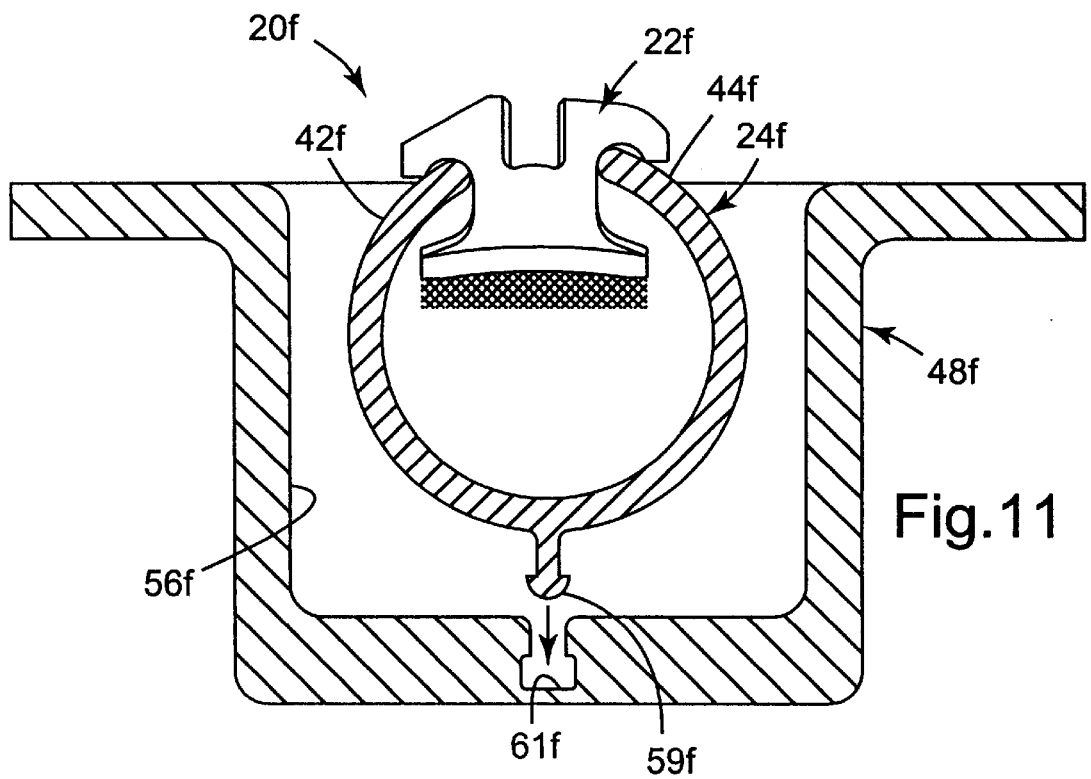
Fig. 11
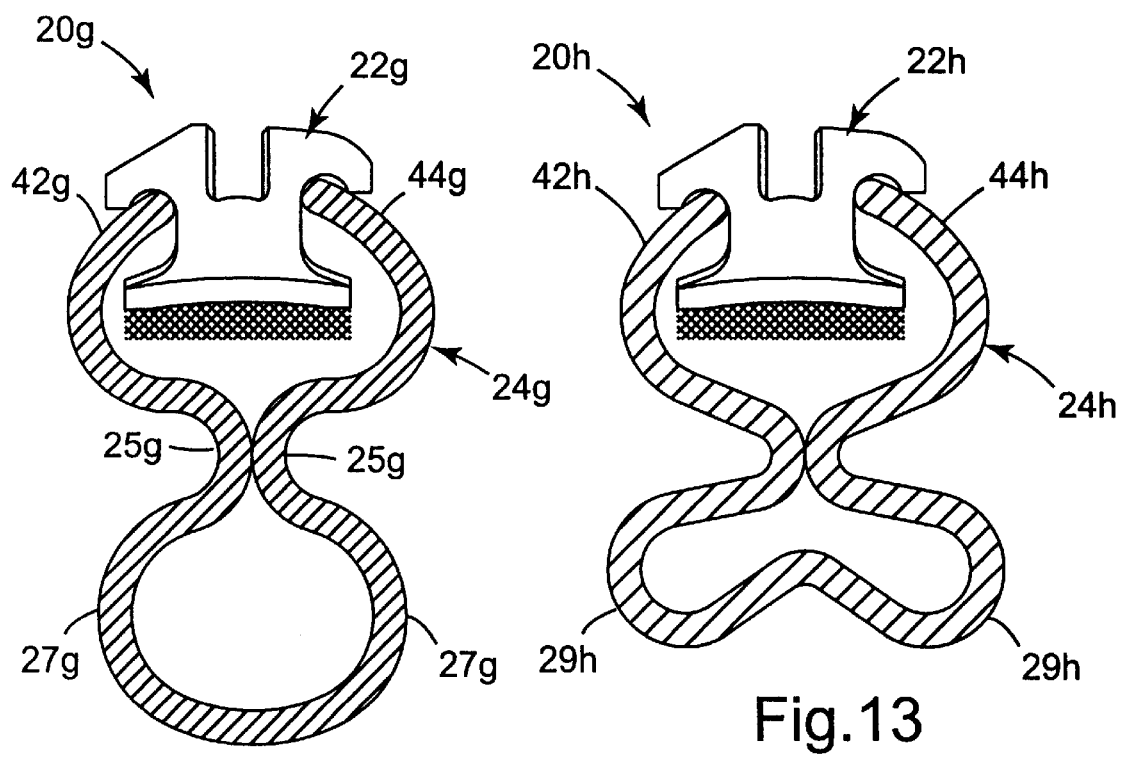
Fig. 12
Fig. 13

CARRIER FOR SUPPORTING ORTHODONTIC BRACKETS

BACKGROUND OF THE INVENTION

1. Field of the Invention

This invention relates to a carrier for supporting brackets of the type used in orthodontic treatment. The carrier is particularly useful for supporting the brackets during their manufacture, during the time that the brackets are received within a container for shipment to an end user and also during the time that the brackets are arranged in a set-up tray in a dental operatory in preparation for application to a patient's tooth surface.

2. Description of the Related Art

Orthodontic treatment involves movement of malpositioned teeth to orthodontically correct positions. Tiny orthodontic appliances known as brackets are connected to exterior surfaces of the patient's teeth, and an archwire is placed in a slot of each bracket. The archwire forms a track to guide movement of the teeth to desired positions for correct occlusion.

In the past, orthodontic brackets were connected to teeth by welding or brazing each bracket to a band that was then placed over the desired tooth in encircling relation. In more recent years, however, it has become common practice to bond orthodontic brackets directly to the surface of the tooth. Brackets that are directly bonded to tooth surfaces provide a more aesthetic appearance than the appearance of brackets that are welded to bands, and help alleviate the problem of a "tinsel tooth" or "metallic mouth" appearance that is often associated with orthodontic treatment.

For many years, it was common practice to apply orthodontic adhesive to the base of directly-bonded brackets immediately before the brackets were placed on the tooth. In some instances, a quantity of adhesive was dispensed onto a mixing pad or dispensing well and a small spatula or other hand instrument was then used to apply a small dab of adhesive to each bracket. In other instances, a quantity of adhesive was dispensed from a syringe directly onto the base of the bracket.

Adhesive precoated brackets are also now available and represent a significant advantage to the orthodontist. Adhesive precoated brackets have a bonding base upon which the manufacturer has applied a precise quantity of adhesive such as a photocurable adhesive. When it is desired to mount the bracket on a tooth, the bracket is simply removed from the package and is placed directly onto the tooth surface.

Examples of adhesive precoated brackets are described in U.S. Pat. Nos. 4,978,007, 5,015,180 and 5,328,363, all of which are assigned to the assignee of the present invention. In certain embodiments of the inventions described in those patents, the bracket and adhesive are packaged in a container that protects the adhesive from light, evaporation, oxidation, contamination, humidity and sublimation. In some of those embodiments, the coating of adhesive on the packaged bracket is in contact with a release liner or coating that helps prevent the adhesive from being disturbed when the bracket is lifted from the package for use.

As can be appreciated, adhesive precoated brackets represent a significant time savings for the orthodontic practitioner because the adhesive need not be carefully applied to the base of each bracket before placement of the bracket onto the patient's tooth. In addition, the manufacturer can control the quantity of adhesive placed on the bracket so that there is sufficient adhesive to substantially fill the space between the bracket base and the tooth when the bracket is pushed into position, and yet there is not an inordinate amount of adhesive that might otherwise require excessive clean-up around the perimeter of the bracket base. Optionally, the adhesive is a light-curable adhesive so that the bracket can be carefully positioned in a proper orientation on the tooth surface before a curing lamp is activated to cure the adhesive and securely fix the bracket in place.

In general, the adhesive used for adhesive precoated brackets that are contained in a package having a release liner or coating are more viscous (i.e. less fluid) than other available orthodontic bonding adhesives, in part to ensure that the adhesive retains its shape and does not separate or distort when the bracket lifted from the package for use. However, some orthodontists prefer the use of less viscous (i.e. more fluid) adhesives in order to facilitate manipulation of the bracket before the adhesive is cured. For example, brackets with less viscous adhesives are relatively easy to slide along the tooth surface when an effort is made align the bracket in a proper, precise orientation on the tooth before the adhesive is cured.

Some practitioners prefer two component chemical-cure adhesives (such as Unite brand adhesive, from 3M Unitek Corporation) over light-curable adhesives. It has been proposed in the past to package orthodontic brackets with one component of a chemical-cure adhesive on each bracket base, and then apply the second component to each bracket base and/or to the patient's tooth once the bracket is removed from the package. Presently, there is a need in the art for an improved package suitable for both chemical-cure adhesives as well as light-curable adhesives.

Moreover, there is increased interest in optimizing the manufacture of orthodontic brackets. Manufacturing optimization may include, for example, automation of the processes for handling of the brackets from the time of manufacture to the time of packaging, as well as increased efficiency of applying the adhesive to the base of the brackets in instances where the brackets are sold with a coating of adhesive. Such improvements in manufacturing can not only reduce costs and processing time, but also may result in a decrease of problems that might otherwise attributed to human error.

SUMMARY OF THE INVENTION

The present invention is directed toward a method and apparatus for supporting orthodontic brackets during manufacture and also while the brackets are received in a shipping container or placed in a set-up tray in the dental operatory. The invention involves the use of a carrier having a tubular member with arms that extend toward each other and engage the bracket in respective recesses located between tiewings of the bracket and the bracket base.

In more detail, the present invention is directed in one aspect to an assembly that includes an orthodontic bracket and a carrier. The orthodontic bracket has a base, a body extending from the base and at least two opposed tiewings extending away from the body. The base and at least one of the tiewings extends past the body in a gingival direction and presents a gingival recess. The base and at least one other of the tiewings extends past the body in an occlusal direction and presents an occlusal recess. The carrier has a tubular member with a pair of arms extending toward each other. Each of the arms has an outer end section, and the outer end sections are spaced apart from each other and present a channel therebetween. The bracket is located in the channel and is supported by the arms with one of the outer end sections extending into the occlusal recess and the other of the outer end sections extending into the gingival recess.

In another aspect, the invention concerns a method of supporting orthodontic brackets and comprises the step of providing a carrier having a tubular member with a pair of arms extending toward each other, wherein each arm includes an outer end section and wherein the outer end sections are spaced apart from each other and present a channel therebetween. The method also includes the step of moving a bracket along the channel until the bracket is located between the outer end sections, with one of the outer end sections received in an occlusal recess of the bracket and the other outer end section received in a gingival recess of the bracket.

These and other aspects of the invention are described in the text that follows as well as in the accompanying drawings.

BRIEF DESCRIPTION OF THE DRAWINGS

FIG. 4 is a side cross-sectional view of one bracket and the carrier illustrated in FIGS. 1 and 2, wherein the carrier is mounted in a container and the container has been received in a chair-side holder for use in the dental operatory;

FIG. 7 is a fragmentary plan view of a carrier according to another embodiment of the present invention;

FIG. 8 is a plan view of a carrier according to yet another embodiment of the invention;

FIG. 10 is a side cross-sectional view of the carriers, the bracket and the tray illustrated in FIG. 9;

FIG. 11 is a perspective cross-sectional view of a carrier and container according to an additional embodiment of the invention;

FIG. 12 is a side cross-sectional view of an assembly that includes a bracket and a carrier according to another embodiment of the invention;

FIG. 13 is a view somewhat similar to FIG. 12 except in accordance with still another embodiment of the invention;

DETAILED DESCRIPTION OF THE PREFERRED EMBODIMENTS

Figure 1:
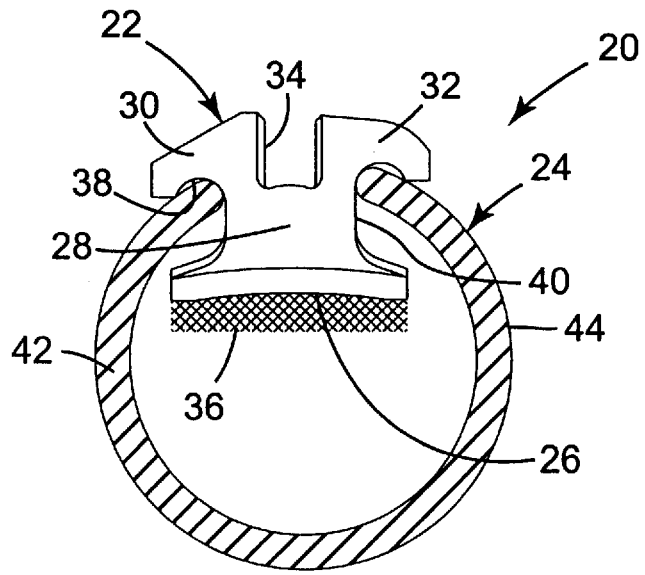
FIG. 1 is side cross-sectional view of an assembly that includes an orthodontic bracket and a carrier for the bracket according to one embodiment of the invention.
Figure 2:
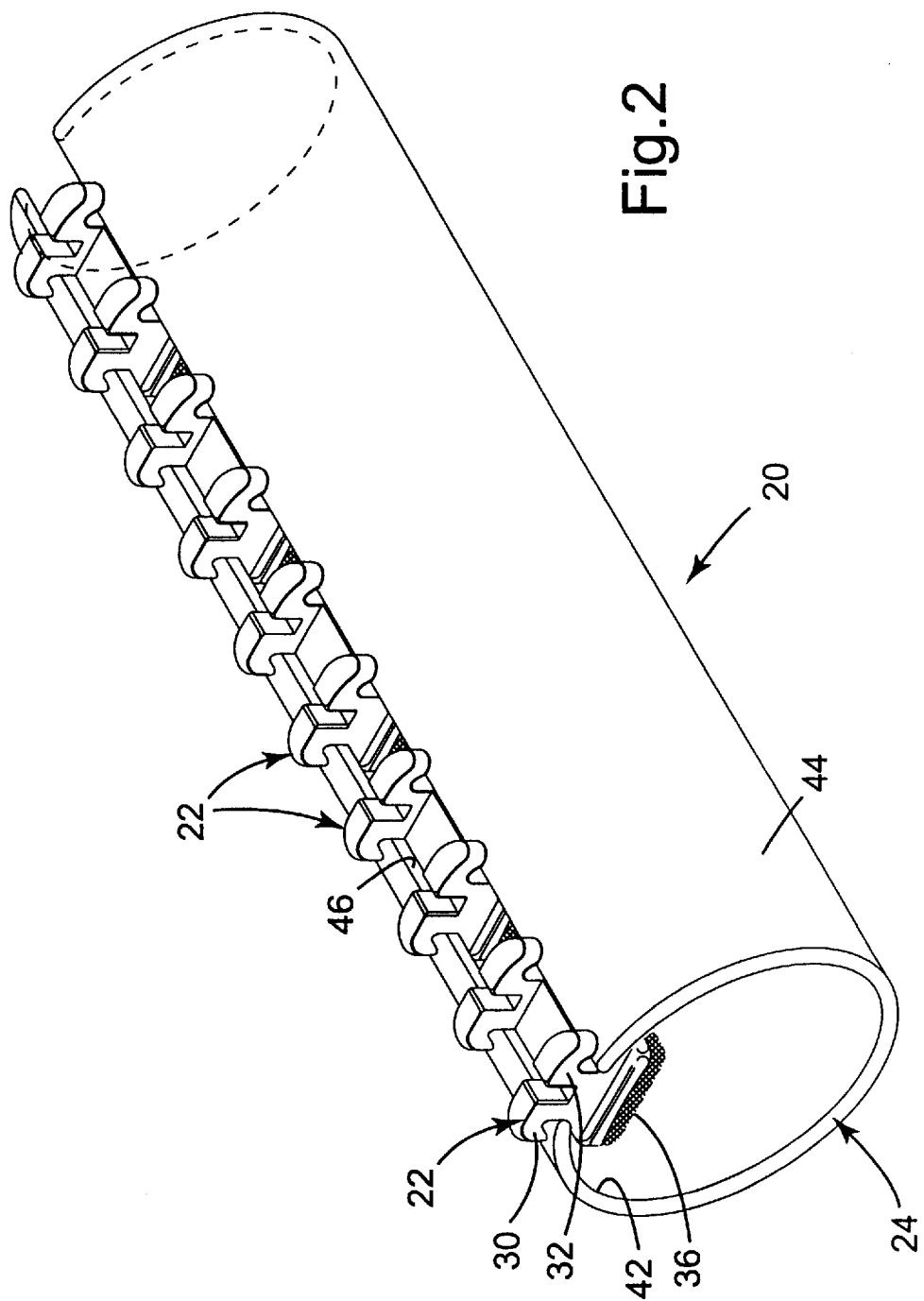
FIG. 2 is a perspective view of the assembly shown in FIG. 1, and illustrating in phantom lines an additional quantity of brackets supported by the carrier.

An orthodontic assembly according to one embodiment of the invention is shown in FIGS. 1 and 2 and is broadly designated by the numeral 20. The assembly 20 includes an orthodontic bracket 22 as well as a carrier 24 for releasably supporting the bracket 22.

The bracket 22 has a tooth-facing base 26 with a compound concave contour that is adapted to match the convex contour of the tooth for which it is intended. A body 28 extends outwardly from the base 26 and at least two tiewings extend away from the body 28. The bracket 22 that is shown in FIGS. 1 and 2 for exemplary purposes is a "twin tiewing" bracket having a pair of spaced apart gingival tiewings 30 that are connected to one side of the body 28 and a pair of spaced apart occlusal tiewings 32 that are connected to an opposite side of the body 28. However, it should be understood in this regard that a "single tiewing" bracket having a single gingival tiewing and a single occlusal tiewing may be used with the assembly 20 as an alternative to the bracket 22 illustrated in the drawings.

Furthermore, the bracket 22 may have a configuration other than that shown in the drawings. For example, the bracket 22 may be angulated and/or be constructed with torque in accordance with selected treatment techniques. The bracket 22 may also be made of any one of a variety of materials, including metal (such as stainless steel), plastic (such as polycarbonate) or ceramic (such as monocrystalline or polycrystalline alumina). If made of plastic or ceramic, the bracket 22 is preferably translucent such that the color of the patient's tooth is visible through the bracket.

An archwire slot 34 is located between the pair of gingival tiewings 30 and the pair of occlusal tiewings 32, and is defined on its lingual side by a labial surface of the body 28. Preferably, although not necessarily, a quantity of orthodontic adhesive 36 extends across the base 26 of the bracket 22 for securing the bracket 22 to an outer surface of the patient's tooth. Preferred adhesives 36 include photocurable adhesives, since such adhesives enable the orthodontist to precisely position the bracket on the tooth at his or her convenience and then activate a light source when desired to cure the adhesive and securely fix the bracket 22 in place.

Suitable photocurable orthodontic adhesives are described, for example, in U.S. Pat. No. 5,575,645 which is incorporated by reference herein. A particularly preferred adhesive is Transbond XT brand adhesive or Transbond LR brand adhesive, both from 3M Unitek Corporation.

The assembly 10 may alternatively include a chemical-cure adhesive such as Unite brand adhesive from 3M Unitek Corporation. In that alternative, one component of the adhesive is preapplied to the base 26 by the manufacturer and a second component is applied by the practitioner once the bracket 22 is removed from the carrier 24. For example, the base 26 may be pressed against a sponge bearing a quantity of the second component, and/or the second component is brushed on the patient's tooth surfaces.

As can be observed by reference to FIGS. 1 and 2, the base 26 of the bracket 22 extends beyond the body 28 in an occlusal and in a gingival direction. A gingival recess 38 is located between the portions of the gingival tiewings 30 and the base 26 that extend beyond the body 28 in a gingival direction, and an occlusal recess 40 is located between the portions of the occlusal tiewings 32 and the base 26 that extend beyond the body 28 in an occlusal direction. The recesses 38, 40 are often provided on conventional orthodontic brackets for use in receiving a ligature such as an elastomeric O-ring or a wire tie that is used to secure the archwire in place in the archwire slot during treatment.

The carrier 24 in the embodiment shown in FIGS. 1 and 2 includes a tubular, cylindrical member with a pair of arms 42, 44 that extend toward each other. Each of the arms 42, 44 has an outer end section, and the outer end section of the arm 42 is spaced apart from the outer end section of the arm 44 to present a channel 46 (FIG. 2) between the arms 42, 44.

The bracket 22 is located in the channel 46 and is supported by the arms 42, 44. As shown in the drawings, the end section of the arm 42 extends into the gingival recess 38 and the end section of the arm 44 extends into the occlusal recess 40. Preferably, the bracket 22 is supported by the arms 42, 44 in such a manner that the base 26 and any adhesive thereon (such as adhesive 36) is spaced from the facing section (i.e., the bottom section when viewing FIG. 1) of the carrier 24. The end sections of the arms 42, 44 may support the bracket 22 by contacting a portion of the body 28 approximately mid-way between the tiewings 30, 32 and the base 26 as shown in FIGS. 1 and 2, or alternatively may support the bracket 22 by contacting the underside of the tiewings 30, 32 (and optionally also contacting an adjacent portion of the body 28) as is likely to occur when the width of the channel 46 is larger than the width of the body 28 or when the bracket 22 is urged in a downwardly direction viewing FIGS. 1 and 2.

Optionally, the carrier 24 has an elongated, central axis and consequently may be used to support a number of brackets such as the bracket 22. Examples of additional brackets 22 are depicted in FIG. 2. The elongated carrier 24 is useful in manufacturing processes for holding the brackets 22 in an aligned array, as may be needed for inspection of the brackets 22, application of ink alignment markings to the brackets 22, or handling of the brackets 22 between manufacturing operations or during packaging. When the carrier 24 is used during manufacturing or packaging operations, it is preferable that the carrier 24 be made of a non-corrosive rigid material such as aluminum or stainless steel that can be re-used many times while satisfactorily withstanding the effects of wear and fatigue.

Figure 3:
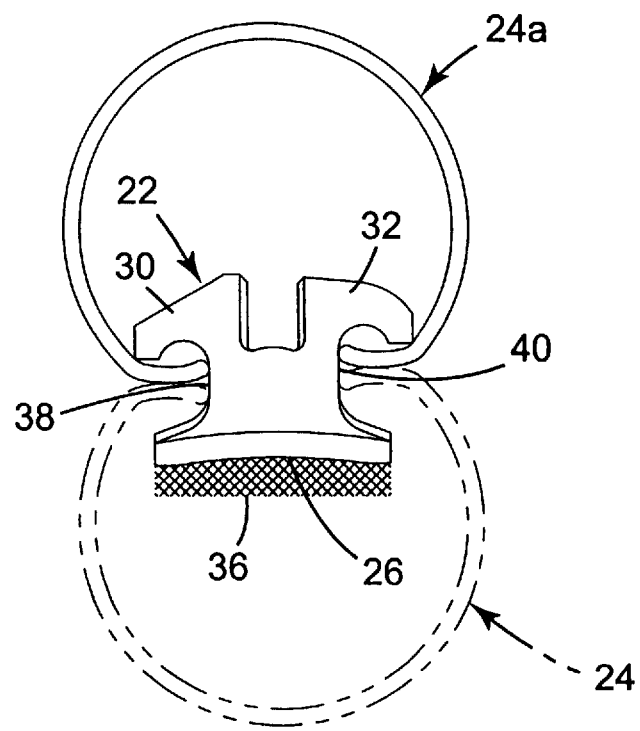
FIG. 3 is a side cross-sectional view of somewhat similar to FIG. 1 but according to another aspect of the invention wherein another carrier has been provided to transfer the brackets from the carrier shown in FIG. 2 and to support the brackets in a somewhat different manner than that which is shown in FIGS. 1 and 2 as may be desirable for certain manufacturing operations.

FIG. 3 illustrates another aspect of the invention, wherein the bracket 22 as described above is received in a channel of a second carrier 24a in an orientation opposite the orientation shown in FIGS. 1 and 2. In FIG. 3, the tiewings 30, 32 of the bracket 22 face the interior of the carrier 24a while the base 26 faces in a direction away from the carrier 24a. Optionally, the carrier 24a is identical to the carrier 24, although as an alternative it may have other configurations or may be provided with couplings for connection to automated processing equipment. Preferably, the carrier 24a is elongated and is of sufficient length to simultaneously support a number of brackets 22.

The use of the carrier 24a as shown in its orientation in FIG. 3 is beneficial for supporting the bracket 22 in a position for certain manufacturing processes, such as for brazing a mesh material to the base 26 or for applying adhesive 36 to the base 26. In one method of use of the carrier 24a, a number of brackets 22 are initially supported by the carrier 24a while the brackets 22 and the carrier 24a are simultaneously moved along the length of the channel 46 of the carrier 24 that is shown in phantom lines if FIG. 3. (Alternatively, the carrier 24 may be moved while the brackets 22 and the carrier 24a remain stationary.) The carrier 24a may then be removed from the brackets 22 by sliding the carrier 24a along the recesses 38, 40 and in a direction parallel to the mesial-distal axes of the brackets 22 until the carrier 24 is disengaged from the brackets 22. In this manner, the brackets 22 are transferred from the carrier 24a to the carrier 24 without losing their orientation relative to each other and without the necessity of handling individual brackets 22 separately.

FIG. 4 is an illustration of the assembly 20 of the bracket 22 and carrier 24 as shown in FIGS. 1 and 2 along with a container 48 and an optional holder 50. Optionally, the carrier 24 has a length along its central axis (i.e. in directions parallel to the direction of view of FIG. 4) that is slightly larger than the mesial-distal width of a single bracket 22, so that the container 48 is used for only one bracket 22. As another alternative, however, the carrier 24 is somewhat longer and supports a number of brackets 22, and the container 48 is correspondingly increased in length to enclose both the carrier 24 and all of the supported brackets 22.

The container 48 includes a substrate 52 and a cover 54 that is releasably connected to the substrate 52. Suitable materials for the substrate 52 and the cover 54 as well as suitable adhesives and other means for releasably fixing the cover 54 to the substrate 52 are described in U.S. Pat. No. 4,978,007.

The substrate 52 includes a well 56 having a central pocket 58 in the shape of a partial cylinder. The pocket 58 has a configuration that matches part of the outer surface of the carrier 24 and is preferably somewhat larger about its periphery than a semi-cylinder in order to receive the carrier 24 in snap-fit relation. Optionally, the carrier 24 may be secured to the pocket 58 by other means such as adhesives, ultrasonic welding and the like.

Preferably, the substrate 52 has a shape such that a top surface of a flange surrounding the well 56 is flush or just slightly below a reference plane that touches labial surfaces of the bracket 22. As a result, the cover 54 snugly engages the bracket 22 when the cover 54 is closed. Free movement of the bracket 22 within the container 48 is substantially hindered until such time as the cover 54 is opened. More preferably, the carrier 24 is in compression between the cover 54 and the pocket 58 when the cover 54 is closed. The carrier 24, the cover 54 and the pocket 58 thereby function as a shock absorber during shipping and handling.

The holder 50 provides convenient structure for supporting the container 48 in a chair-side tray, shelf or other location near the patient in the dental operatory. Preferably, the holder 50 is sufficiently large to support a number of containers such as the container 48, so that all of the brackets selected by the orthodontist for use on a single patient are conveniently carried by a single holder 50. For example, the holder 50 may include structure for supporting two rows of containers identical to the container 48, with ten brackets in each row so that a sufficient number of brackets are provided for all of the desired teeth according to typical orthodontic treatment procedures.

As shown in FIG. 4, the holder 50 has a groove 60 that receives and supports the container 48. Optionally, the substrate 52 has flexible outwardly extending legs 62 that are received in undercut corners of the groove 60 in snap-fit relation in order to releasably secure the container 48 to the holder 50. As other alternatives, however, the container 48 may be coupled to the holder 50 by releasable adhesives or double-sided adhesive tape, or by other structure such as hook and loop fasteners.

To remove the bracket 22 from the container 48, the cover 54 is lifted from the substrate 52 to expose the well 56. Next, the orthodontic practitioner grasps the bracket 22 by its mesial and distal sides using, for example, a pair of tweezers or other suitable hand instrument and moving the bracket 22 in an upwardly direction (viewing FIG. 4) away from the bottom of the container 48. As the bracket 22 is lifted, the outer end sections of the carrier arms 42, 44 engage the labial side of the bracket base 26, and further upward movement causes the arms 42, 44 to deflect outwardly in directions away from each other. Additional movement of the bracket 22 in an upwardly direction causes the arms 42, 44 to spread apart and enlarge the channel 46 to a dimension that is equivalent to the occlusal-gingival width of the bracket base 26, so that the bracket 22 can then be pulled completely free of and disengage the carrier 24.

In the embodiment shown in FIG. 4, the carrier 24 is preferably made of a flexible material that can readily deform to allow spreading movement of the arms 42, 44 and yet have sufficient resilience and rigidity to hold the bracket 22 securely against the underside of the cover 54 when the cover 54 is closed. Preferred materials for the carrier 24 include, for example, polyethylene or polypropylene. Optionally, the arms 42, 44 of the carrier 24 are provided with lines of weakness 64 such as grooves, perforations, slits, apertures or recesses on either or both of their interior and exterior surfaces, to facilitate spreading and folding back of the arms 42, 44 when the bracket 22 is lifted from the container 48. The lines of weakness 64 may cause the material to fracture, or alternatively may facilitate stress of the material past its yield point as the arms 42, 44 are moved apart. The lines of weakness 64 hinder return movement of the arms 42, 44 to their orientation shown in FIG. 4 and preferably prevent substantially all such return movement. As another option, however, the carrier 24 may be made of a dead-soft material such as aluminum. The lines of weakness 64 or, alternatively, the dead-soft material help ensure that the arms 42, 44 do not engage and disturb the adhesive 36 as the bracket 22 is removed from the container 48.

Figure 6:
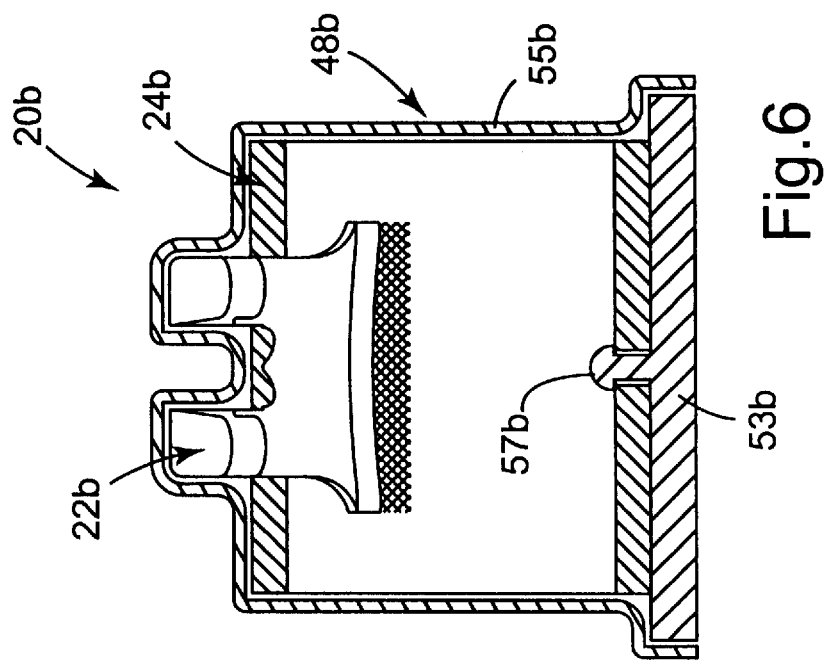
FIG. 6 is an end cross-sectional view of the bracket, carrier and container assembly depicted in FIG. 5.
Figure 5:
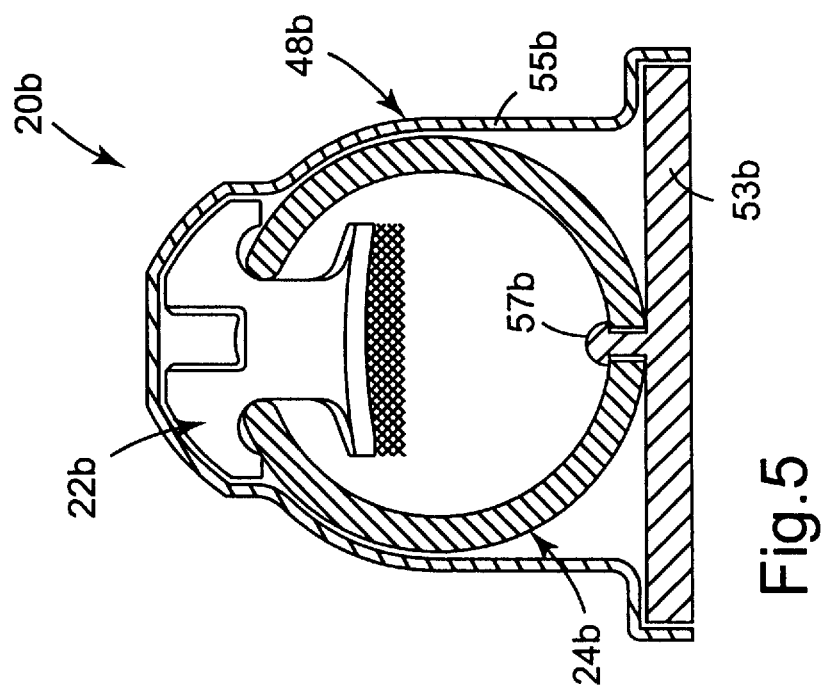
FIG. 5 is a view of an orthodontic bracket and carrier assembly according to another embodiment of the invention, wherein the carrier includes at least one aperture and a container surrounding the carrier and the bracket includes a peg received in the aperture.

FIGS. 5 and 6 show another embodiment of the invention, wherein an assembly 20b includes an orthodontic bracket 22b and a carrier 24b. The bracket 22b is identical to the bracket 22 described above. The carrier 24b is identical to the carrier 24, except that a bottom portion of the carrier 24b (viewing FIGS. 5 and 6) includes an aperture that is optionally circular.

The assembly 20b also includes a container 48b having a base 53b and a barrier 55b connected to the base 53b. The base 53b is preferably relatively rigid and includes an upstanding peg 57b that extends through the aperture on the bottom of the carrier 24b. The top of the peg 57b includes an enlarged head that is bigger than the aperture in order to securely connect the carrier 24b to the base 53b. The head of the peg 57b could be formed, for example, by an ultrasonic welding operation or by a heated platen.

Preferably, the barrier 55b is a vacuum formed or heat sealed over the bracket 22b and the carrier 24b as well as the base 53b in order to hinder movement of the bracket 22b relative to the carrier 24b. The barrier 55b may be made of a thin plastic sheet material such as polyester film that can be readily cut or fractured when desired to remove the bracket 22b. Optionally, the barrier 55b is made of a material such as described in U.S. Pat. No. 4,978,007 that transmits light in the visible spectrum and yet is substantially opaque to actinic radiation. As such, the bracket 22b is visible through the barrier 55b in order to check the contents of the assembly 20b, and yet the photocurable adhesive on the bracket 22b will not unduly cure before such time as the container 48b is opened.

The apertures of the carrier 24b provide an advantage during manufacture. When such apertures are spaced at regular intervals along the length of the carrier 24b, the apertures provide a convenient series of holes for sprocket tractor feed systems as may be utilized in moving the bracket 22b from one processing station to another, or from a processing station to a packaging station. Further, more than one aperture may be provided for each corresponding bracket 22b, and the apertures may be of shapes other than circular in order to facilitate securing the carrier 24b to a transport device in the factory or to the base 53b of the container 48b. If desired, the apertures can provide automated feedback to a computer or controller as to the position of each bracket 22b along the manufacturing line and can serve to count the number of brackets 22b that have passed a certain location along the manufacturing line.

FIG. 7 depicts an orthodontic assembly 20c according to another embodiment of the invention. The assembly 20c includes one or more brackets 22c (three brackets 22c are shown in FIG. 7) that are substantially identical to the brackets 22. The carrier 24c is identical to the carrier 24b with the exceptions as described below.

As illustrated in FIG. 7, the carrier 24c has a channel 46c with a series of rectangular notches 47c that are optionally located opposite respective apertures 49c. Each notch 47c corresponds in shape to the perimeter configuration of the bracket body and provides a nest to receive and support the respective bracket 22c. The notches 47c complementally engage the bracket body and hinder unintentional sliding movement of the brackets 22c along the channel 46c.

Another embodiment of the invention is illustrated in FIG. 8, wherein an orthodontic assembly 20d includes a series of orthodontic brackets 22d, each of which is essentially identical to the bracket 22 described above. The assembly 20d also includes a carrier 24d that is similar to the carriers 24, 24b and 24c with the exceptions as described below.

In more detail, the carrier 24d includes a series of slits or relief areas 51d located along each side of the channel 46d. As such, arms 42d, 44d of the carrier 24d are segregated into arm portions 43d that deflect and move somewhat independently of movement of adjacent arm portions 43d. The relief areas 51d facilitate removal of a selected one of the brackets 22d, without unduly spreading the arms 42d, 44d to such an extent that adjacent brackets 22d located along the channel 46d might otherwise move from their intended location.

Figure 9:
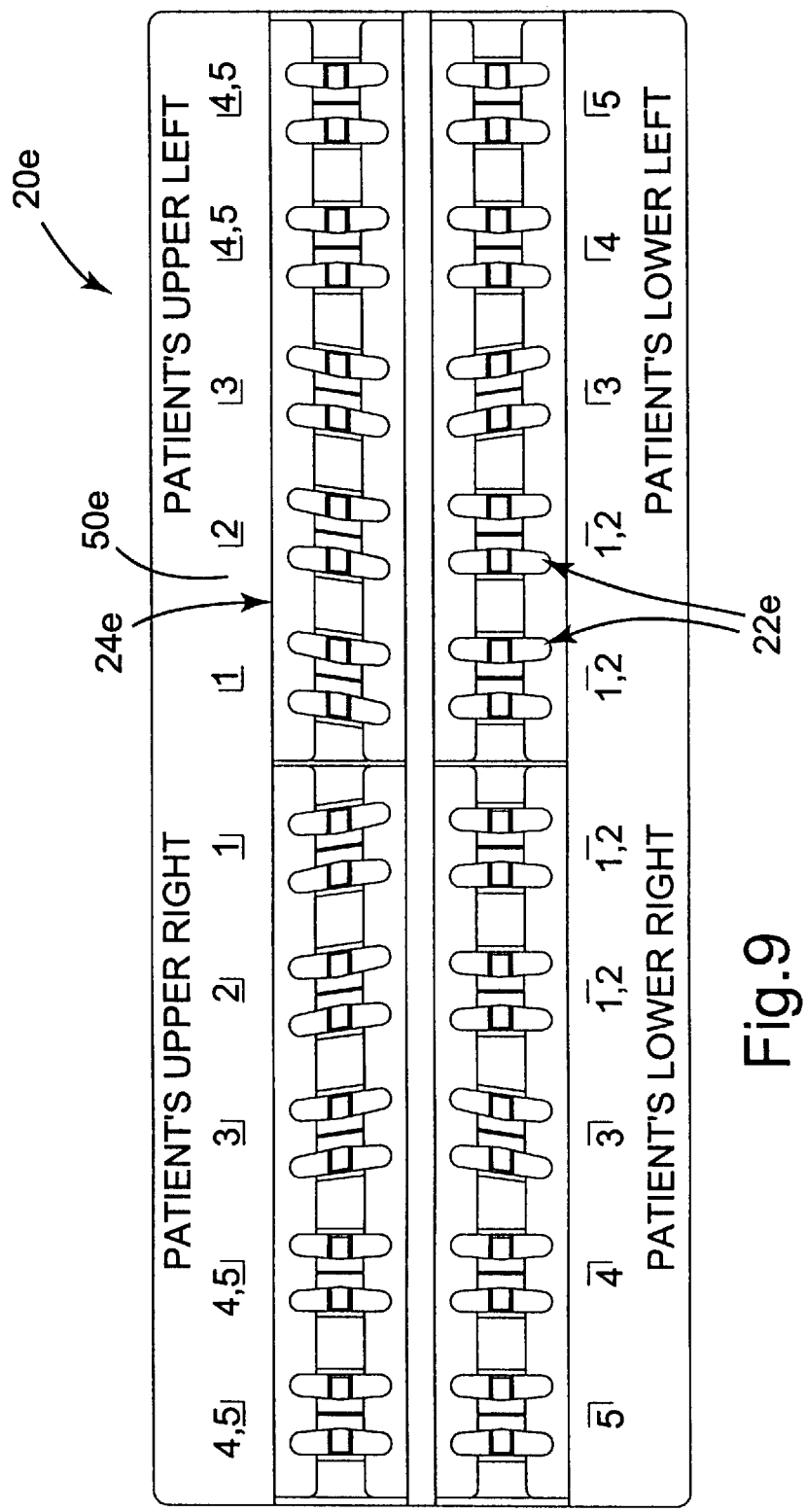
FIG. 9 is a plan view of a pair of carriers and a number of brackets received in the carriers according to a further embodiment of the invention, wherein the carriers are received in a chair-side tray.

FIGS. 9 and 10 illustrate an assembly 20e according to yet another embodiment of the invention. The assembly 20e includes a series of orthodontic brackets 22e that are received in carriers 24e. The assembly 20e also includes a chair-side set-up tray or holder 50e having two elongated, parallel, side-by-side grooves.

The brackets 22e are similar to the brackets 22 described above. The carrier 24e is somewhat similar to the carrier 24d shown in FIG. 8, except that the carrier 24e has a rectangular configuration in directions transverse to its longitudinal axis as can be appreciated by reference to FIG. 10. The two grooves of the holder 50e matingly receive the carriers 24e and securely hold the latter in place. The carriers 24e may be secured in the holder 50e by double-sided adhesive tape with a releasable adhesive, or by mating dovetail shapes of the carriers 24e and the grooves 50e that provide a snap-fit, secure connection.

The brackets 22e are released from the carrier 24e by grasping the mesial and distal sides of the brackets 22e with a hand instrument and lifting the bracket 22e in a direction away from the holder 50e. Alternatively, the brackets 22e may be sequentially released from the carrier 24e by sliding each bracket 22e along the length of the channel and toward an open end of the carrier 24e.

The assembly 20e that is depicted in FIGS. 9 and 10 represents a set or case of brackets as may be useful for a single patient. Preferably, the carriers 24e with selected brackets 22e are shipped to the orthodontist who then places the carriers 24e in the appropriate grooves of the holder 50e. As an alternative, the carriers 24e may be placed in the holder 50e by the manufacturer and shipped with the holder to the practitioner. In either instance, the carriers 24e are preferably placed in a hermetically sealed container that is opaque to actinic radiation before shipment to the practitioner in order to extend the shelf life of the light-curable adhesive and help keep the brackets 22e free of dust and other contaminants. Optionally, a stop member such as a section of low adhesion adhesive tape is placed across each end of the channel of each carrier 24e to help preclude the brackets 22e from sliding along the channel and inadvertently disengaging from the carrier 24e.

The orthodontic assembly 20f that is shown in part in FIG. 11 includes a carrier 24f that is somewhat similar to the carrier 24, except that the carrier 24f has a key 59f that extends in a direction parallel to the central axis of the carrier 24f and to the mesial-distal axis of a bracket 22f (that is identical to the bracket 22). The key 59f is located on the bottom of the carrier 24f and is remote from ends of arms 42f, 44f.

A container 48f for receiving the carrier 24f includes a well 56f having a keyway 61f. The key 59f is received in the keyway 61f in snap-fit relation, and is precluded from rotating relative to the keyway 61f due to its elongated and rectangular configuration in plan view (not shown). Although remaining components of the container 48f, it should be understood in this regard that such components may be similar or identical to corresponding components set out in the embodiments described above.

An orthodontic assembly 20g as shown in FIG. 12 includes an orthodontic bracket 22g and a carrier 24g. Except as described below, the bracket 22g and the carrier 24g are essentially identical to the brackets and carriers described above.

The carrier 24g has somewhat "FIG. 8"-shaped configuration, with opposed sides of the carrier 24g touching each other as shown at the locations 25g. When the practitioner squeezes the convex, bulbous sides of the carrier 24g at the locations designated by the numeral 27g, opposed sides of the carrier 24g pivot about the engagement points 25g and tend to spread arms 42g, 44g in order to facilitate removal of the bracket 22g from the carrier 24g.

The orthodontic assembly 20h depicted in FIG. 13 is somewhat similar to the orthodontic assembly 20g, except that a lower portion of a carrier 24h has two diverging sections as indicated by the numerals 29h. When the sections 29h are squeezed together by the practitioner's fingers, arms 42h, 44h of the carrier 24h tend to spread apart and facilitate disengagement and removal of the bracket 22h from the carrier 24h.

Figure 14:
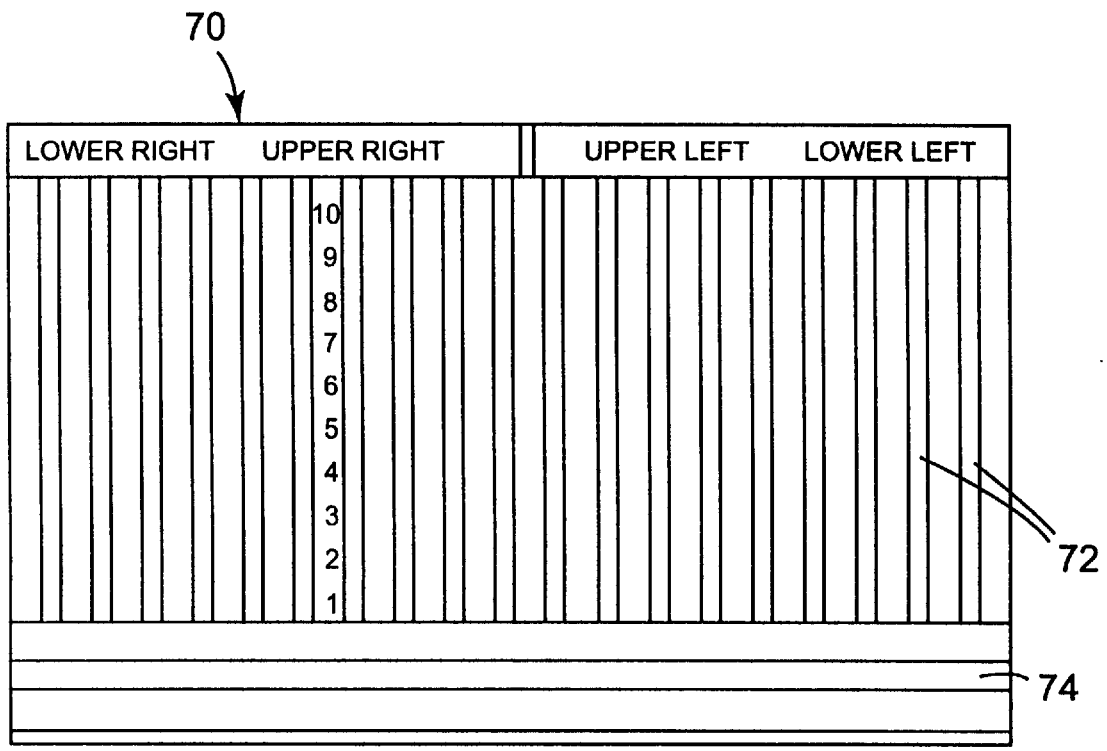
FIG. 14 is a front elevational view of a stand especially suitable for use with certain of the carriers described above.
Figure 15:
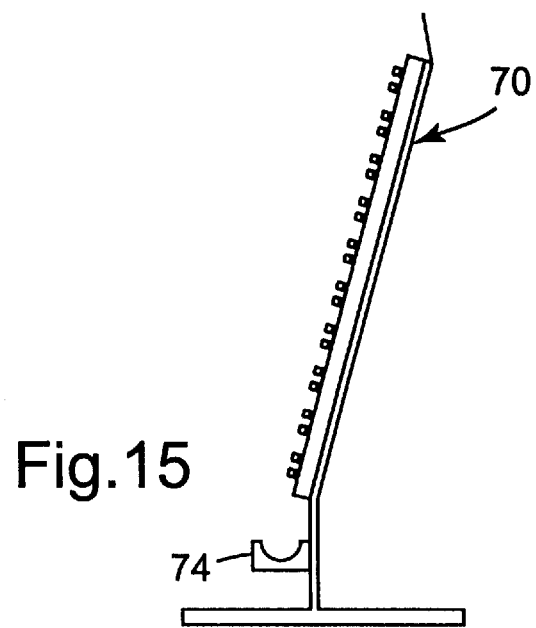
FIG. 15 is a side elevational view of the stand shown in FIG. 14.

FIGS. 14 and 15 illustrate a stand 70 that is particularly useful with the orthodontic assemblies described above. The stand 70 includes a number of channels 72 (see FIG. 14) that extend in parallel upright directions and each channel 72 is adapted to releasably receive a carrier supporting a number of brackets (shown only in FIG. 15). The stand 70 provides a convenient inventory dispensing system so that the user can readily determine how many brackets are on hand. Optionally, a cutter (not shown) is coupled to the stand 70 for cutting the carrier between adjacent brackets for custom tray set-ups. The cut portion of the carrier along with the bracket then drop to the underlying trough 74. As another option, the brackets move freely along the channels of the carriers so that as a bracket is removed from the lowermost end of each carrier the remaining brackets in the carrier slide downwardly until the next adjacent bracket reaches the lowermost end.

Optionally, structures such as a proximity sensor are associated with each channel 72 and connected to a computer in order to determine the amount of brackets remaining in each carrier. Moreover, the carriers could include bar codes that are scanned to provide information to the computer, so that the practitioner may readily determine both the quantity and identity of the brackets in inventory. Such structure can be used to determine usage habits and facilitate re-ordering of the brackets when necessary.

A variety of modifications to the assemblies described above may be apparent to those skilled in the art without departing from the spirit of the invention. Accordingly, the invention should not be limited to the currently preferred embodiments that are described in detail above, but only by a fair reading of the claims that follow along with their equivalents.

We claim:

1. An assembly including:
   an orthodontic bracket having a base, a body extending from said base and at least two opposed tiewings extending away from said body, said base and at least one of said tiewings extending past said body in a gingival direction and presenting a gingival recess, said base and at least one other of said tiewings extending past said body in an occlusal direction and presenting an occlusal recess; and
   a carrier having a tubular member with a pair of arms extending toward each other, each of said arms having an outer end section, said outer end sections being spaced apart from each other and presenting a channel therebetween, said bracket being located in said channel and being supported by said arms with one of said outer end sections extending into said occlusal recess and the other of said outer end sections extending into said gingival recess.

2. The assembly of claim 1 wherein said arms are flexible.

3. The assembly of claim 1 wherein said arms are movable away from each other to enable release of said bracket.

4. The assembly of claim 3 wherein said arms are flexible and include lines of weakness to facilitate movement away from each other.

5. The assembly of claim 3 wherein said arms are flexible and moved past their yield point when moved away from each other during release of said bracket.

6. The assembly of claim 1 wherein said member has a generally "C"-shaped configuration.

7. The assembly of claim 1 wherein said member has a generally "FIG.-8"-shaped configuration with said arms being located at the top of said configuration.

8. The assembly of claim 1 and including an adhesive extending across said base of said bracket.

9. The assembly of claim 1 and including a container having a well that receives said carrier and said bracket, said carrier having a substrate said container including a cover extending across said well and in contact with said bracket.

10. The assembly of claim 9 wherein said cover has a shape that matches the shape of at least a portion of said tiewings including curved portions of said tiewings.

11. The assembly of claim 9 wherein said arms are flexible and wherein said cover presses against said bracket with sufficient force to deflect said arms in a direction away from said cover.

12. The assembly of claim 9 and including a hermetic seal between said cover and said substrate.

13. The assembly of claim 9 and including a repositionable adhesive between said cover and said substrate.

14. The assembly of claim 9 wherein one of said substrate and said carrier includes a key and wherein the other of said substrate and said carrier includes a keyway that matingly receives said key.

15. The assembly of claim 14 wherein said keyway receives said key in snap-fit relation.

16. The assembly of claim 14 wherein said keyway comprises a hole located in said carrier at a position remote from said bracket.

17. The assembly of claim 1 wherein said carrier is elongated and including a number of additional brackets each having a gingival recess and an occlusal recess in contact with said outer end sections of said arms.

18. The assembly of claim 17 wherein said carrier includes a relief area between adjacent brackets.

19. The assembly of claim 17 and including a holder supporting said carrier in an orientation such that each bracket may be removed from the carrier by sliding each bracket along said channel.

20. The assembly of claim 17 and including a second carrier having a channel and arms with outer end sections facing said channel of said second carrier, said outer end sections of said second carrier being in contact with said gingival recess and said occlusal recess of at least some of said brackets.

21. The assembly of claim 1 wherein said base of said bracket faces away from said carrier.

22. The assembly of claim 1 wherein said tiewings of said bracket face away from said carrier.

23. The assembly of claim 1 wherein said channel, said occlusal recess and said gingival recess have approximately equal lengths.

24. The assembly of claim 1 wherein said carrier has a flat bottom section remote from said channel.

25. A method of supporting orthodontic brackets comprising the steps of:

providing a carrier having a tabular member with a pair of arms extending toward each other, wherein each arm includes an outer end section, and wherein the outer end sections are spaced apart from each other and present a channel therebetween; and moving a bracket along the channel until the bracket is located between the outer end sections, with one of the outer end sections received in an occlusal recess of the bracket and the other outer end section received in a gingival recess of the bracket.

26. The method as set out in claim 25, and including the step of providing a number of additional brackets and a second carrier having a tabular member with a channel, and moving the second carrier relative to the brackets in order to position the brackets along the channel of the second carrier.

27. The method of claim 25 including the step of removing a bracket from the channel by sliding the bracket along the channel.

28. The method of claim 25 including the step of removing a bracket from the channel by spreading the arms a sufficient distance apart from each other to enable the bracket to disengage the carrier.

* * * * *

UNITED STATES PATENT AND TRADEMARK OFFICE
CERTIFICATE OF CORRECTION

PATENT NO.: 5,827,058

DATED: October 27, 1998

INVENTOR(S): John S. Kelly, Russell A. Jordan and Randall E. Adam

It is certified that error appears in the above-identified patent and that said Letters Patent is hereby corrected as shown below:

Col. 9, Line 46 "FIG.-8" should be ---figure-8---.

Col. 10, Line 57 "FIG.-8" should be ---figure-8---.

Col. 10, Line 63 insert a comma after the word "substrate".

Col. 12, Line 10 "tabular" should be ---tubular---.

Signed and Sealed this

Twenty-seventh Day of March, 2001

*Attest:*

NICHOLAS P. GODICI

*Attesting Officer*     Acting Director of the United States Patent and Trademark Office